United States Patent [19]
Lambert et al.

[11] Patent Number: 5,151,231
[45] Date of Patent: Sep. 29, 1992

[54] METHOD FOR MAKING LIQUID CRYSTALLINE TUBE HAVING A POINT

[75] Inventors: James M. Lambert, Centerville; Donald D. Solomon, Spring Valley, both of Ohio

[73] Assignee: Becton, Dickinson and Company, Franklin Lakes, N.J.

[21] Appl. No.: 765,782

[22] Filed: Sep. 26, 1991

Related U.S. Application Data

[62] Division of Ser. No. 495,072, Mar. 19, 1990, Pat. No. 5,078,700.

[51] Int. Cl.⁵ .............................................. B29C 47/20
[52] U.S. Cl. .................................. 264/108; 264/162; 264/209.3; 264/296; 264/323; 264/328.12; 264/331.21
[58] Field of Search ............. 264/209.1, 209.3, 331.21, 264/108, 320, 328.12, 323, 162, 176.1, 296; 604/264; 425/144, 380; 128/772

[56] References Cited

U.S. PATENT DOCUMENTS

| | | | |
|---|---|---|---|
| 4,325,903 | 4/1982 | Wissbrun et al. | 264/176.1 |
| 4,581,399 | 4/1986 | Yoon | 264/331.21 |
| 4,614,629 | 9/1986 | Economy et al. | 264/328.12 |
| 4,661,300 | 4/1987 | Daugherty | 425/144 |
| 4,838,877 | 6/1989 | Massau | 604/264 |
| 4,843,109 | 6/1989 | Bailey et al. | 264/328.12 |
| 4,851,503 | 7/1989 | Matsumoto et al. | 264/176.1 |
| 4,867,174 | 9/1989 | Skribiski | 128/772 |
| 4,904,433 | 2/1990 | Williamitis | 264/320 |

*Primary Examiner*—Jeffery Thurlow
*Attorney, Agent, or Firm*—Richard E. Brown

[57] ABSTRACT

A catheter assembly includes a tubing portion and a needle portion, at least one of which is a thermoplastic liquid crystalline polymer. The tubing and needle may be integral or unitary. The invention includes a method to make the assembly in which a melt of the liquid crystalline polymer is shear thinned by passing through an orifice such as an extrusion die to make tubing. The shear thinned melt may be directed into a mold having a point to make a liquid crystalline needle.

6 Claims, 2 Drawing Sheets

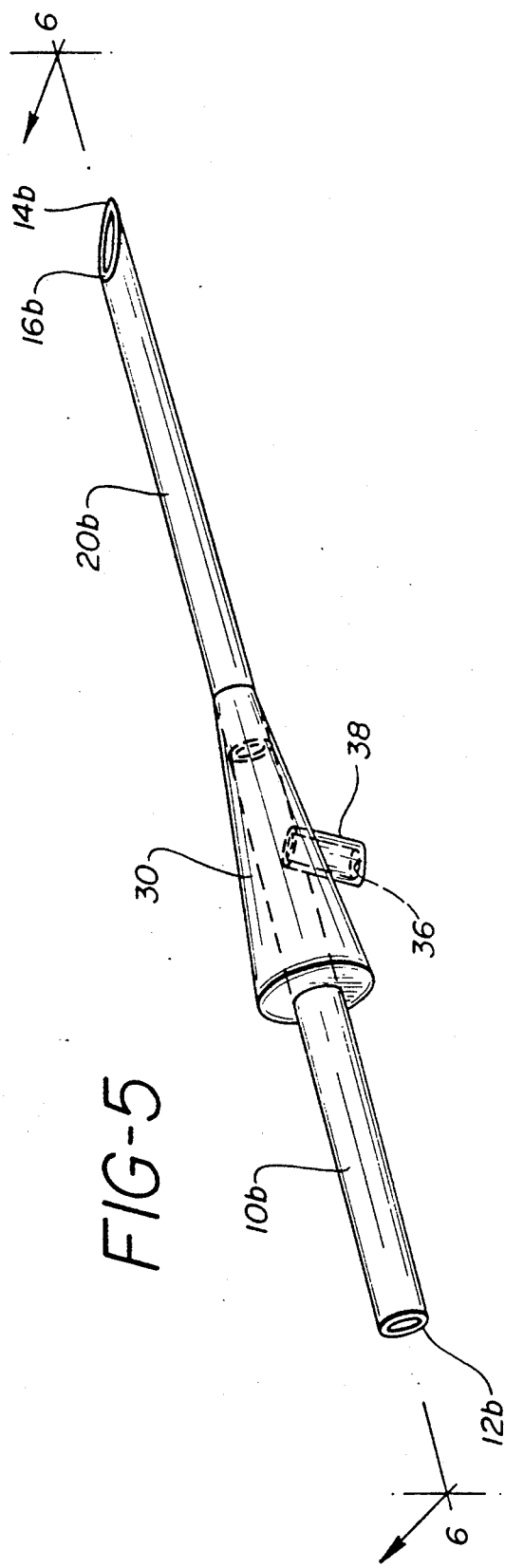
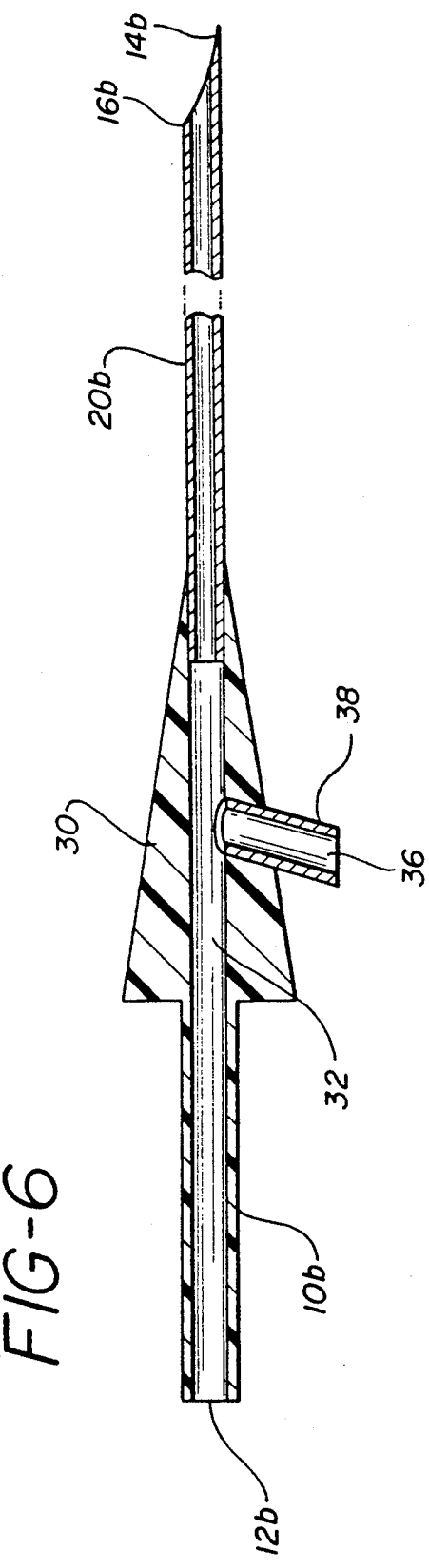

METHOD FOR MAKING LIQUID CRYSTALLINE TUBE HAVING A POINT

This is a division of application Ser. No. 07/495,072, filed Mar. 19, 1990 now U.S. Pat. No. 5,078,700 issued Jan. 7, 1992.

BACKGROUND OF THE INVENTION

1. Field of the Invention

This invention relates to a plastic medical article and more particularly relates to a catheter of improved mechanical properties.

2. Background of the Invention

Substances which exhibit physical properties characteristic of a transition state between conventional liquids and solid are generally termed liquid crystals. The transition state is believed to be a result of an ordering of the molecules in melts and solutions of various organic compounds that occurs within certain ranges of temperature. The ordering is sufficient to impart some solid-like properties to the substances, but the forces of attraction usually are not strong enough to prevent flow. On the other hand, in those cases where a liquid crystalline substance is substantially solid in terms of flow, there are other fluid aspects of its physical state. This duality of physical properties is expressed in the term liquid crystallinity, or the synonymous term mesomorphism.

Some polymers are also known to exhibit liquid crystalline properties. These products have been disclosed for various applications, most particularly for molded parts which require high impact strength and for temperature sensing, recording and display devices. Representative of such disclosures are U.S. Pat. No. 4,814,211 to Buckley et al. and U.S. Pat. No. 4,841,014 to Brodowski.

Catheterization procedures conventionally include puncture of a patient's skin and insertion of a catheter into a body cavity, such as the blood stream, using some type of catheter insertion device. For maximum patient comfort, it is essential that the puncturing tip be as sharp as possible. It is also highly desirable that the catheter, and perforce any insertion equipment, be of the smallest possible cross-sectional area during insertion and use. It is nevertheless evident that the catheter lumen must be large enough to achieve the required rate of administration of a medicament solution through the catheter. Furthermore, for many applications, catheters are of great length and are extended along rather tortuous and extended paths within the body to reach desired locations. Accordingly, the ideal catheter would be stiff enough for insertion and manipulation inside a vein or artery without kinking, but at the same time be sufficiently soft and nonbrittle to avoid breaking off.

Catheters of the prior art have generally been made of polymeric materials such as polystyrene, polycarbonate, polyurethane and polyacrylate. These materials, while providing advantages for certain catheter applications, nevertheless have mechanical properties which limit their use for other applications. Accordingly, there is a need for a catheter having a balance of strength, stiffness and nonbrittleness suitable for insertion into a patient and maneuverability after insertion. The present invention addresses this need.

SUMMARY OF THE INVENTION

A catheter assembly includes a tubing portion and a needle portion for penetration of a patient's skin, at least one of the tubing and needle portions being of a thermoplastic liquid crystalline polymer. The tubing and needle portions may be a single integral liquid crystalline catheter molded to include a point, and the tubing portion may include a hub portion. Alternatively, the needle portion may be a metal needle affixed to the liquid crystalline tubing, or it may be a liquid crystalline needle having a point affixed to a tubing of either liquid crystalline polymer or non-liquid crystalline polymer.

Any thermotropic liquid crystalline polymer which undergoes molecular orientation on shear thinning and retains the orientation on cooling may be extruded into the tubing of the invention. In the present disclosure, the term shear thinning describes the well-known propensity of most polymer melt to undergo reduction in viscosity when subjected to conditions of high shear. Preferred liquid crystalline polymers shear-thin to a viscosity of 500 poise or less and thereby flow into and fill completely the point of a hollow needle mold. Most preferred are liquid crystalline polyesters.

The invention includes a method to prepare tubing by extruding shear thinned liquid crystalline polymers and a method to prepare hollow needles and catheters having a point by passing a melt of liquid crystalline polymer through an orifice to effect shear thinning and directing the shear thinned melt into a hollow tubing mold which has a point.

Molecularly oriented liquid crystalline polymers have high impact strength, high flex or bend modulus and low elongation. These properties make them admirably suited for fabrication into plastic articles having a point for skin penetration without danger of bending or breaking. Further, the pointed articles can be made in a single molding operation because melts of the polymers shear thin to a viscosity low enough to flow into and completely fill a mold including a point. A particularly useful article is a tubing having a molded point which may serve as a catheter without the need for a separate catheter inserter.

The catheter tubing of the invention may be of very thin wall so that a lumen large enough to provide adequate fluid flow can be obtained in a catheter of narrow outside diameter for patient comfort. Because the wall is thin, the high flex modulus is overcome sufficiently to allow the catheter to be threaded through tortuous pathways without breaking, kinking or needing a guide wire.

Liquid crystalline polymers have some radiopaquing properties for visualization after insertion, but also are compatible with conventional radiopaque agents, such as bismuth oxide, for formulations of higher radiopaque visibility.

Ease of manufacture by simple extrusion and molding operations provides economy for both the manufacturer and user, a distinct advantage for medical articles designed for the single use market favored today.

BRIEF DESCRIPTION OF THE DRAWINGS

FIG. 5 is a perspective view of a catheter-needle-hub assembly of the invention; and FIG. 6 is a sectional view of the assembly of FIG. 5 taken along the line 6—6 thereof.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the invention, a catheter which is at least partially fabricated of a liquid crystalline polymer comprises a tubing open at both ends. The catheter may include a point for penetration of a patient's skin. In one embodiment of the invention, the tubing may be entirely of a liquid crystalline polymer molded to include a point so that a separate catheter inserter is not needed. In a second embodiment, a liquid crystalline polymeric tubing may be used with a separate needle portion which includes the point. In this embodiment of the invention, the needle may be a conventional stainless steel needle or may be of the same or a different liquid crystalline polymer. In still another embodiment of the invention, a liquid crystalline polymeric needle may be used with a tubing of a non liquid crystalline polymer.

The catheter of the invention will now be described with reference to the drawings wherein like numerals are used with a letter suffix to designate like parts throughout.

Figure 1:
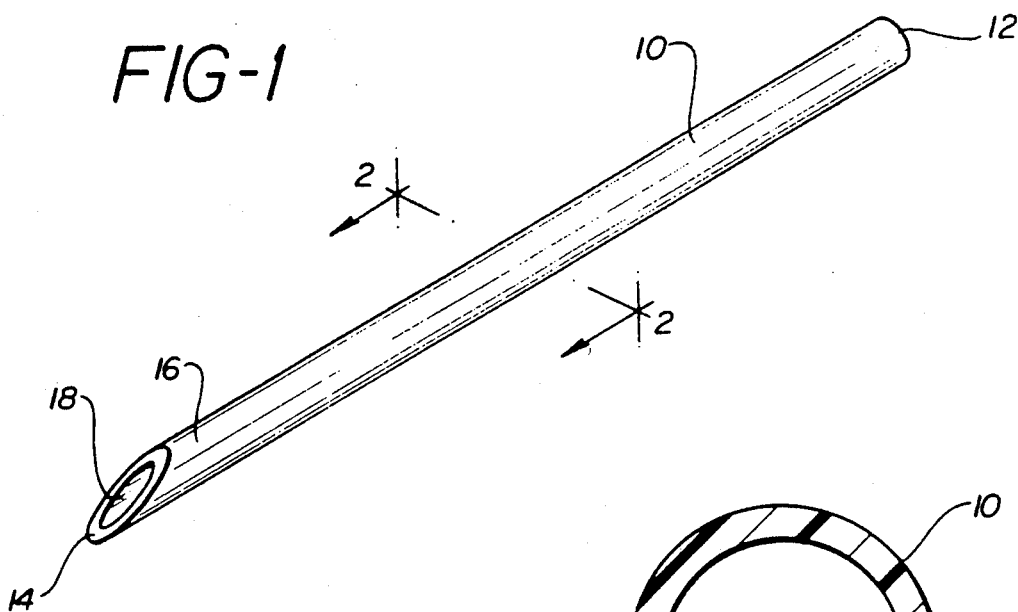
FIG. 1 is a perspective view of a catheter of the invention.
Figure 2:
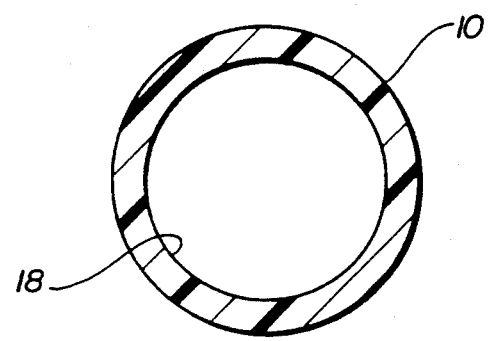
FIG. 2 is a sectional view of the catheter of FIG. 1 taken along the line 2—2 thereof.

One embodiment of the invention, illustrated in FIGS. 1 and 2, includes a tubing 10 having a first open end 12 for connection to, for example, a medicament reservoir (not shown). Tubing 10 tapers to a point 14, preferably beveled, and also has a second open end 16. Tubing 10 defines a lumen 18 as illustrated in FIG. 2.

Figure 3:
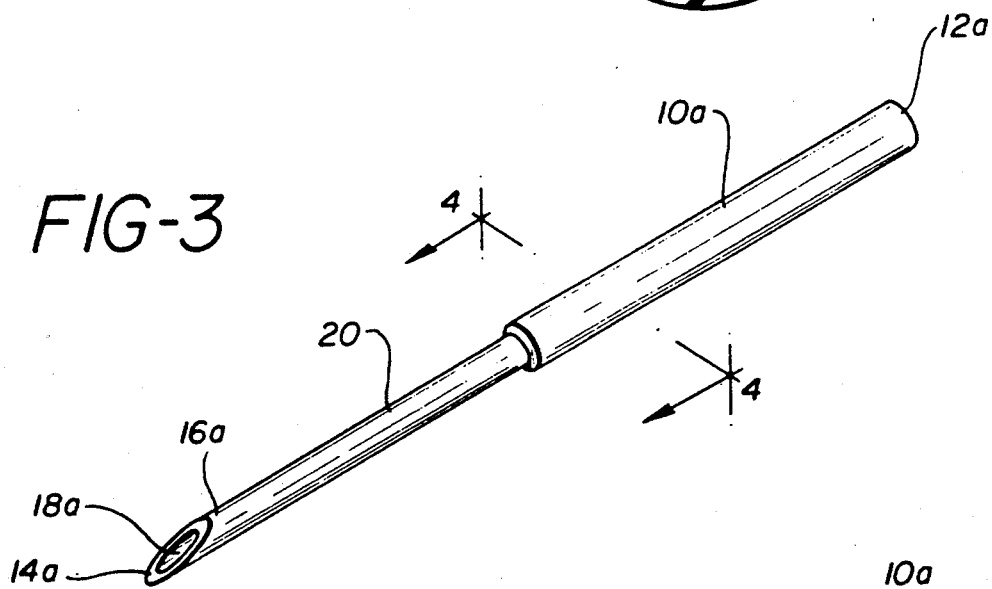
FIG. 3 is a perspective view of a catheter assembly of the invention which includes a needle.
Figure 4:
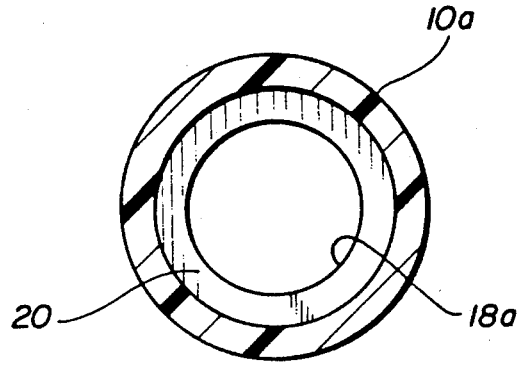
FIG. 4 is a sectional view of the assembly of claim 3 taken along the line 4—4 thereof.

FIGS. 3 and 4 illustrate a catheter of polymeric tubing 10a having open end 12a. Tubing 10a is affixed to a needle 20 having open end 16a and point 14a, preferably beveled. Tubing 10a and needle 20 define a lumen 18a.

The liquid crystalline polymeric tubing may be connected to a hub. The hub and tubing may be separate components conventionally attached, as by glue, wherein the hub may be of the same or different liquid crystalline polymer or the hub may be of a non-liquid crystalline polymer. Preferably, the hub and tubing are integrally molded of liquid crystalline polymer. FIG. 5 and 6 show liquid crystalline tubing 10b integrally molded with hub 30. Hub 30 has a passageway 32 therethrough which provides fluid communication between tubing 10b and a needle 20b. While hub 30 is shown to be conical, it may be of any shape convenient for conventional attachment to needle 20b and may include other integrally molded parts, such as tabs, lugs or threads (not shown) which may be useful for attachment to the needle. The hub may also include an optional port 36 and associated projection 38 for attaching a second tubing (not shown).

Various conventional methods, such as gluing may be used for attaching separate needle and tubing components. Preferably the needle is inserted inside of the tubing by an interference fit.

Any thermoplastic polymer of elongated molecular shape which can exist in a liquid crystalline phase is contemplated to fall within the scope of this invention. Exemplary of, but not limited to, polymer classes which can form liquid crystals are polyethers, polyphosphazines, polyxylylenes, polysulfones, polyamides, polysiloxanes and polyesters. Preferred liquid crystalline polymers for molding into the catheter of the invention are polyesters having a plurality of aromatic rings which contribute to ordering or alignment of the elongated molecules. The aromatic rings may be connected directly together, as in biphenyl moieties, or they may be separated by a connecting unit, as exemplified by generic structures I and II.

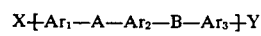

In structures I and II $Ar_1$, $Ar_2$ and $Ar_3$ may be an aromatic, heterocyclic or substituted aromatic ring such as phenyl, pyridyl, naphthyl, biphenyl or quinolyl wherein the substituent may be a halogen or lower alkyl group. A and B may be alkyl, alkyloxy, alkyldioxy, oxygen, sulfur, sulfone, carbonyl, oxycarbonyl, alkylcarbonyl, alkyloxycarbonyl, alkylcarbonyloxy and oxyalkylcarbonyl wherein at least one of A and B is an oxycarbonyl group, the term alkyl being about 1 to 5 carbon atoms, X and Y may be hydroxyl or carboxyl and groups X,Y,A and B may be in a meta or para relationship or, if Ar is a naphthylene or quinoline ring, the bonds to A and B may be in a 2,6; 2,7; 3,6; 3,7; or 4,8 relationship.

Some liquid crystalline polymers suitable for the present invention are commercially available, such as Vectra TM (Hoechst-Celanese, Chatham, N.J., Xydar TM and Torlon TM (Amoco Performance Products, Ridgefield, Conn., and LCP TM (RTP Co., Winona, Minn.). Representative structures of preferred liquid crystalline polymers are

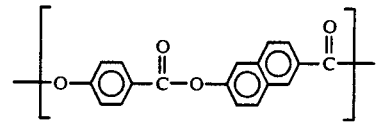

p-oxybenzoate-6-oxy-2-naphthoate copolymer

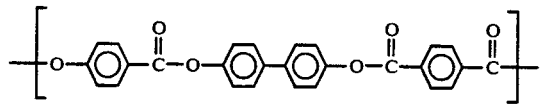

p-oxybenzoate-biphenol terephthalate copolymer

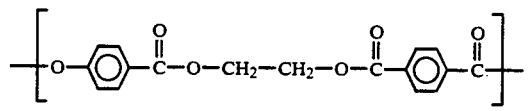

p-oxybenzoate-polyethylene terephthalate copolymer

Synthesis of the preferred crystalline polyesters used in the invention may be carried out by well-known esterification and transesterification procedures. For example, hydroxyaromatic acids, such as hydroxy benzoic acid, hydroxynaphthoic acid and hydroxybiphenyl carboxylic acid may be polymerized or copolymerized. Aromatic dicarboxylic acids, such as terephthalic acid, isophthalic acid, naphthylene dicarboxylic acid and biphenyl dicarboxylic acid may be polymerized with aromatic glycols, such as dihydroxybenzene, dihydroxynaphthylene and dihydroxybiphenyl, araliphatic glycols, such as p-hydroxy benzyl alcohol, or with aliphatic glycols, such as ethylene glycol. Aliphatic dicarboxylic acids, such as succinic acid, may be polymerized with aromatic glycols such as hydroquinone. Representative procedures are given by Calundann, et al., "Anisotropic Polymers, Their Synthesis, and Properties," Proceedings of the Robert A. Welch Conference on Chemical Research, . XXVI, Synthetic Polymers, (1982) and by Chung et al., *Polymer Engineering and Science* 26, 901 (1986).

Melts of polymeric liquid crystallines are known to have a degree of molecular organization whereas melts of ordinary polymers exist in an almost completely random state. Organization of the molecules of both ordinary polymers and liquid crystalline polymers is greatly enhanced by shear thinning. As is known in the art, shear thinning is due to orientation of the elongated polymer molecules into an arrangement in which the molecules are aligned substantially completely in the direction of melt flow through an orifice. While most polymers undergo more or less shear thinning, conventional polymers such as polypropylene or polyethylene do not retain their orientation on cooling, but rather undergo molecular randomization and thereby lose the mechanical properties gained when their melts are shear thinned. In contrast, a shear thinned liquid crystalline polymer melt, having filled a mold, retains its molecular orientation on cooling, and it is the oriented molecules in the cooled polymer which gives the molded product the unique combination of properties characteristic of liquid crystalline polymers.

The catheter tubing of the invention may have a gauge size of from 8 to 26. Preferred tubing is of 14 to 20 gauge.

Applicants have also discovered that the liquid crystalline polymer melt, on passing through an orifice, shear thins to a viscosity which allows the polymer to flow into and fill a long, thin mold including a point. Thus, the invention includes a hollow plastic article having a point sufficiently sharp to penetrate a patient's skin without substantial discomfort. Preferred hollow articles are catheters and needles which may have a point of any desired shape. While the most preferred hollow article is a catheter which has a beveled point for maximum patient comfort, it is evident that a hollow plastic needle may also find application in a variety of other areas, such as liquid transfer for example with a hypodermic needle attached to a syringe. A particularly attractive application of liquid crystalline needles is in magnetic resonance imaging (MRI), a non-invasive diagnostic technique which uses apparatus which includes a very high field magnet. Oftentimes needles which must be nonmetallic are used to biopsy areas highlighted by the MRI.

When the catheter of the invention includes a liquid crystalline needle used with a non-liquid crystalline polymer, suitable polymers are, for example, polypropylene, polytetrafluoroethylene, polyurethane, polyethylene terephthalate and the like.

In accordance with the invention, liquid crystalline polymers after extruding into tubing or molding into hollow needles, have high impact strength. Thus, the tensile at break of the molded or extruded liquid crystalline polymer may be about 10,000 to 70,000 psi, preferably about 25,000 to 35,000 psi. Elongation at break may be about 1 to 50, preferably about 2 to 10%. The flex modulus may be about 1,000,000 to 20,000,000, preferably about 3,000,000 to 7,000,000 psi. For polystyrene, a product totally unsuitable because of its brittleness, these values are about 6,000 psi, 2% and 480,000 psi respectively.

In accordance with the present invention, it has been found that a liquid crystalline polymer melt is suitable for molding into the inventive devices having a sharp point if it has a viscosity of no more than about 500 poise. Preferred liquid crystalline polymers have a shear-thinned viscosity of about 75 to 150 poise. Such products have a very low coefficient of friction, generally in the range of 0.1 to 0.25. This property enables the article of the invention to release from the mold without any mold releasing agents.

The catheter tubing of the invention may be fabricated from a thermoplastic liquid crystalline polymer by conventional means. A mandrel may be alternately dipped into a melt or solvent solution of the polymer and dried, the process being repeated until the tubing is of the desired thickness. A preferred method for forming a tubing is by conventional melt and solution extrusion processes well known to one skilled in the art wherein shear thinning takes place when the melt or solution passes through the extrusion die. A liquid crystalline homopolymer may be extruded, or a solution or melt of a mixture of liquid crystalline polymers may be extruded. If desired, two or more polymers may be coextruded using conventional equipment giving a tubing having a base layer and one or more laminated layers. Such a tubing may present different surfaces to the body environment and any liquid passing through the tubing.

Thus, in another aspect of the invention, a method to prepare hollow liquid crystalline polymeric needles is provided. In its broadest scope, the method includes melting a thermotropic liquid crystalline polymer and introducing the melt into an injection mold of the desired shape in a conventional molding operation. Molding may be performed at any temperature between the melting and decomposition temperatures of the polymer at which the viscosity of the melt is sufficiently low to enable the melt to completely fill the mold. Preferably, the polymer may be melted to its anisotropic melt range and processed while within this range.

In a preferred method of the invention, the polymer melt may be forced under pressure through an orifice and thence directly into the mold. Passage of the melt through the orifice effects shear thinning and reduces the viscosity of the melt to facilitate completely filling of the mold.

The degree of shear thinning of a polymer is a function of the nature of the polymer, the temperature, the pressure applied (and thus the rate of passage through the orifice) and the size of the orifice. These variables are well-known in the injection molding art, and a suitable combination of thinning and molding conditions may easily be determined by those skilled in the art. Thus, without wishing to be limited thereby, suitable molding parameter ranges are a pressure of 500 to 1,500 psi, a shear rate of 10 to 150 $\sec^{-1}$, and an orifice size of 0.5 to 2.0 mm. After shear thinning, the polymer melt flows into and completely fills the mold, including the tip.

After release from the mold, the molded point of the article is generally sharp enough to puncture a patient's skin without substantial discomfort. If desired, however, the molded point may be machined by any conventional procedure such as grinding or sanding, or may be thermoformed in a heated tipping die to further sharpen the point.

The finished article may then be sterilized by any convenient procedure, such as heat, irradiation, or chemical methods taking advantage of the known stability of liquid crystalline polymers to these techniques.

The low friction surface of the point of the article of the invention in many cases allows skin puncture without any lubricant. In contrast, conventional stainless steel needles have a coefficient of friction of about 0.57, and often are lubricated prior to puncture of a patient's skin, as, for example, with a polysiloxane lubricant.

EXAMPLE

Polyester liquid crystalline polymer (Vectra®) was melted and forced at a temperature of 290° C. under a pressure of 900 psi through a die having a circular orifice of 1.6 mm diameter. The die was mounted on a conventional injection molding apparatus so that the polymer, after passing through the orifice, flowed directly into a tubing mold shaped to include a beveled point. After filling, the mold was cooled and the tubing was removed. It was found that the tubing had a point which was comparable in penetration force to a stainless steel lancet (Becton, Dickinson and Company).

What is claimed is:

1. A method for preparing a liquid crystalline polymeric tubing having a point comprising:
   a) heating a thermotropic liquid crystalline polymer to give a melt having a viscosity of 500 poise or less;
   b) directing said melt into a tubing mold which includes a point whereby said melt completely fills said mold;
   c) cooling said melt in said mold whereby said melt solidifies to a tubing having the shape of said mold; and
   d) removing said tubing from said mold.

2. The method of claim 1 wherein said liquid crystalline polymer is selected from the group having structures I and II $$X + Ar_1 - A - Ar_2 - B - Ar_3 + Y \quad \text{I}$$

$$X + Ar_1 - A - Ar_2 + Y \quad \text{II}$$

wherein $Ar_1$, $Ar_2$ and $Ar_3$ are independently selected from the group consisting of an aromatic ring and a hetercylic ring, A and B are independently selected from the group consisting of alkyloxy, alkyldioxy, oxygen, sulfur, sulfone, carbonyl, oxycarbonyl, alkylcarbonyl alkyloxycarbonyl, alkylcarbonyloxy and oxyalkylcarbonyl wherein at least one of A and B is an oxycarbonyl group, the term alkyl being 1 to 5 carbon atoms, and X and Y are selected from the group consisting of hydroxy and carboxyl.

3. The method of claim 1 wherein said melt is passed through an orifice under pressure prior to said directing step.

4. The method of claim 1 further comprising machining said point to further sharpen said point.

5. The method of claim 1 further comprising thermoforming said point in a heated tipping die to further sharpen said point.

6. A method for preparing a liquid crystalline polymeric tubing comprising:
   a) heating a thermotropic liquid crystalline polyester to give a melt;
   b) forcing said melt under pressure through an orifice whereby the viscosity of said melt decreases to about 500 poise or less;
   c) directing said melt of reduced viscosity into a tubing mold which includes a point whereby said melt completely fills said mold;
   d) cooling said melt in said mold whereby said melt solidifies to a tubing having the shape of said mold; and
   e) removing said tubing from said mold.

* * * * *